(12) United States Patent
Huang et al.

(10) Patent No.: US 9,714,284 B2
(45) Date of Patent: Jul. 25, 2017

(54) ANTIBODIES AND METHOD FOR DETERMINING DELETIONS IN HBV PRE-$S_2$ REGION

(71) Applicant: NATIONAL HEALTH RESEARCH INSTITUTES, Miaoli County (TW)

(72) Inventors: Wenya Huang, Tainan (TW); Ih-Jen Su, Miaoli County (TW); Yun-Ping Lee, Tainan (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 14/333,346

(22) Filed: Jul. 16, 2014

(65) Prior Publication Data
US 2015/0072885 A1 Mar. 12, 2015

Related U.S. Application Data

(60) Provisional application No. 61/846,764, filed on Jul. 16, 2013.

(51) Int. Cl.
| | | |
|---|---|---|
| *C12N 7/00* | (2006.01) |
| *C07K 16/08* | (2006.01) |
| *G01N 33/574* | (2006.01) |
| *G01N 33/576* | (2006.01) |

(52) U.S. Cl.
CPC ....... *C07K 16/082* (2013.01); *G01N 33/5764* (2013.01); *G01N 33/57438* (2013.01); *C07K 2317/34* (2013.01); *G01N 2800/085* (2013.01); *G01N 2800/50* (2013.01); *G01N 2800/54* (2013.01)

(58) Field of Classification Search
None
See application file for complete search history.

(56) References Cited

U.S. PATENT DOCUMENTS

| 6,022,543 | A | 2/2000 | Thoma | |
|---|---|---|---|---|
| 7,785,586 | B2 * | 8/2010 | Jolivet-Reynaud .. | C07K 16/082 424/130.1 |
| 2007/0184476 | A1 | 8/2007 | Hsieh et al. | |
| 2010/0047764 | A1 | 2/2010 | Krupka | |

FOREIGN PATENT DOCUMENTS

| AU | 628156 | | 9/1992 | |
|---|---|---|---|---|
| DE | WO 88/10301 | * | 6/1988 | ............. C12N 15/00 |
| WO | WO2013/002449 A1 | | 1/2013 | |

OTHER PUBLICATIONS

Honorati et al. (WJG, Apr. 1998, p. 464-466).*
Colson et al. (Virology, 2007, p. 30-40).*
Accession No. Q75TL5_HBV 2006.*
Zhang et al., Whole genome HBV deletion profiles and the accumulation of preS deletion mutant during antiviral treatment, *BMC Microbiol.* 2012; 12:1-10.
Tsai HW et al., A Clustered Ground-Glass Hepatocyte Pattern Represents a New Prognostic Marker for the Recurrence of Hepatocellular Carcinoma After Surgery, *Cancer*, 2011; 117:2951-2960.
Chen CH et al., Pre-S deletion and complex mutations of hepatitis B virus related to advanced liver disease in HBeAg-negative, *Gastroenterology.* 2007; 133:1466-1474.
Shen FC et al., A pre-S gene chip to detect pre-S deletions in hepatitis B virus large surface antigen as a predictive marker for hepatoma risk in chronic hepatitis B virus carriers, *J Biomed Sci.* 2009; 16:84-91.
Larry T. Mimms, et al., "Discrimination of Hepatitis B Virus (HBV) Subtypes Using Monoclonal Antibodies to the PreS1 and PreS2 Domains of the Viral Envelope", Virology, vol. 176, pp. 604-619, 1990.
Sadakazu Usuda, et al., "Serological detection of hepatitis B virus genotypes by ELISA with monoclonal antibodies to type-specific epitopes in the preS2-region product", Journal of Virology Methods, vol. 80, pp. 97-112, 1999.

* cited by examiner

*Primary Examiner* — Agnieszka Boesen
(74) *Attorney, Agent, or Firm* — Muncy, Geissler, Olds & Lowe, P.C.

(57) ABSTRACT

A HBS-specific antibody, a LHBS-specific antibody, a WT LHBS-specific antibody, an immunoassay kit comprising the antibodies, and a method of detecting pre-$S_2$ deletion mutant LHBS using the immunoassay kit are disclosed herein. The method comprises incubating a biological sample with a first antibody to captured HBS proteins; detecting the LHBS and WT LHBS bound to the immobilized first antibody, respectively; and calculating the amount of the pre-$S_2$ deletion mutant LHBS protein by subtracting the amount of the WT LHBS protein from that of the LHBS protein. Advantageously, by the method described herein, the amount of the pre-$S_2$ deletion mutant LHBS, a potential high-risk marker for HCC incidence in chronic HBV carriers and recurrence in HCC patients after hepatectomy surgery, in a biological sample may be easily calculated without mutual influence between the WT and pre-S mutant LHBS while reducing the labor-intensive process for cloning each gene product before analysis.

18 Claims, 7 Drawing Sheets

ANTIBODIES AND METHOD FOR DETERMINING DELETIONS IN HBV PRE-$S_2$ REGION

CROSS-REFERENCE TO RELATED APPLICATION

This application claims the benefit of U.S. Provisional Application No. 61/846,764, filed on Jul. 16, 2013, the disclosure of which is incorporated herein in its entirety by reference.

BACKGROUND OF THE INVENTION

1. Field of the Invention

The present invention generally relates to anti-hepatitis B virus surface protein antibodies, immunoassay kit comprising the same and method of detecting hepatitis B virus surface proteins, in particular to a hepatitis B virus surface protein-specific antibody, a large hepatitis B virus surface protein-specific antibody, a wild type large hepatitis B virus surface protein-specific antibody, an immunoassay kit comprising the antibodies, and a method of detecting pre-$S_2$ deletion mutant large hepatitis B virus surface protein.

2. Description of the Related Art

Chronic hepatitis B virus infection is a major cause of hepatocellular carcinoma (HCC) worldwide and its most important cause in Asia. Hepatitis B virus (HBV)-related HCC often occurs at the age of 40 or older, suggesting that HBV may persist in carriers for decades before HCC actually develops. It is important for long-term monitoring high-risk markers in chronic HBV carriers to identify the ones that need frequent follow-up or uptake prophylactic therapies. In addition, development of high-risk recurrence markers in HCC patients receiving hepatectomy surgery is also important for clinicians to identify the ones with relatively worse prognosis, who need to uptake aggressive treatments. Though up to now the methods (e.g. ultrasound) and tumor markers (e.g. alpha-fetal protein) to diagnose HCC have been established, the high-risk markers for HCC incidence and recurrence have not been fully identified, given that HCC tumorigenesis is a complex process regulated by various crosstalks between host and viral factors.

Figure 1:
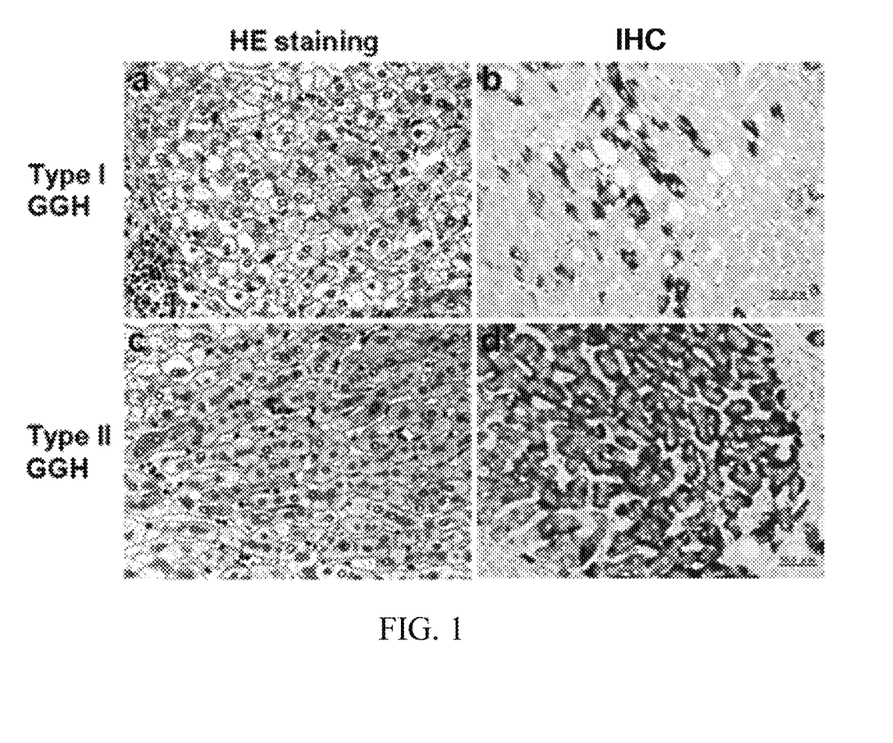
FIG. 1 is a schematic view of GGH and the expression patterns of hepatitis B virus surface antigen. Type I GGH are usually scattered singly (a, hematoxylin-eosin [HE] stain× 200) and express an inclusion-like pattern of the surface antigen (b, immunohistochemical [IHC] stain for the surface antigen). Type II GGH consistently cluster in nodules (c) and express a marginal pattern of the surface antigen (d).
Figure 2:
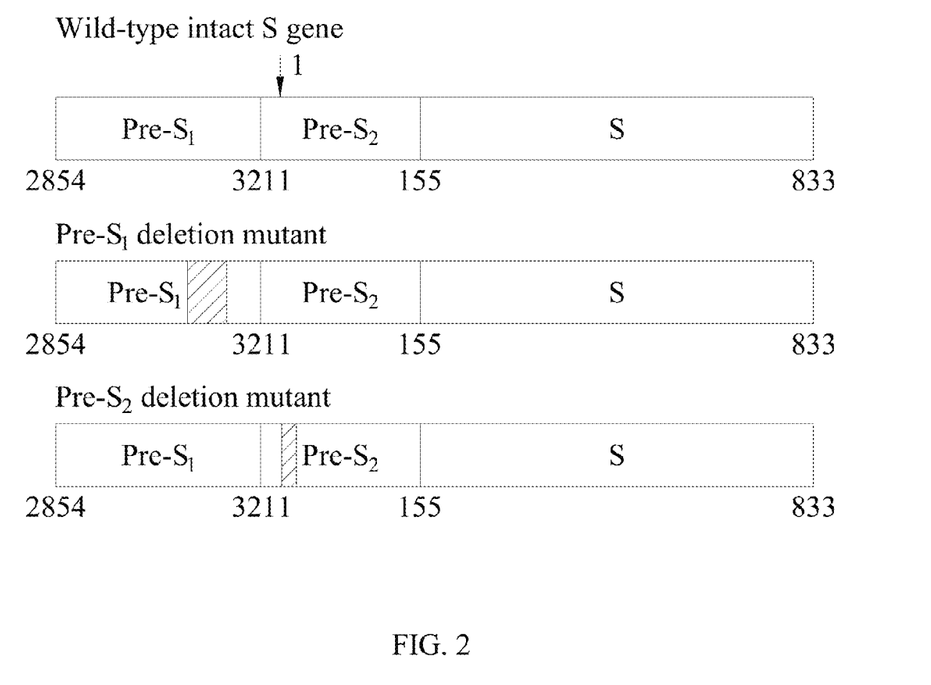
FIG. 2 is a schematic view of the wild-type, pre-S$_1$ and pre-S$_2$ mutant LHBS gene. The shaded boxes are the regions deleted in the pre-S1 and pre-S$_2$ mutant LHBS, respectively. The numbers labeled on the bottom of the gene are to indicate the regions of the pre-S$_1$, pre-S$_2$ and S regions of the gene in nucleotide sequences of HBV genome. The arrow on top of the diagram indicates the start (nt. 1) of the HBV genome.

The pre-$S_2$ deletion mutant large hepatitis B virus surface protein (LHBS), isolated from the type 2 ground glass hepatocyte (GGH), is highly associated with HCC (1). GGH is prevalent in livers with chronic HBV infection and HBV-induced HCC tumors. Type I GGH are usually scattered singly in the hepatic lobules with the expression of dense homogeneous or "inclusion-like" pattern of HBS. This type of GGH usually appears starting at the early carrier stage or in patients with active diseases, frequently co-expresses with a nuclear or cytoplasmic core antigen (2,3). Previous studies found that type I GGH harbors the LHBS partially deleted of the pre-$S_1$ region and accumulates in ER lumen (4). On the other hand, type II GGH expresses a unique pattern of HBS at the cell margin or periphery (For GGH morphologies, see FIG. 1). Most interestingly and importantly, this type of GGH consistently clusters in nodules and usually appear at the advanced or low replicative stages of virus replication, and are frequently associated with cirrhosis or HCC, which suggests that type II GGH may represent clonally-proliferated, adenomatous, or preneoplatic lesions of HCC (2,3). By dissecting the cirrhotic nodules containing type II GGH, the HBV genomes were clonally proliferated and integrated, supporting the concept of a clonal or adenomatous lesion of type II GGH. This type of GGH displays a unique pattern of "marginal" type surface antigens and harbors the LHBS partially deleted of the pre-$S_2$ region, designated pre-$S_2$ mutant LHBS (3). The pre-$S_2$ mutant LHBS is highly expressed in most of the HBV-induced cirrhotic nodules through the stages of the pre-neoplastic lesions, early HCC, and large HCC tumors, which implies the important role of pre-$S_2$ mutant LHBS in the tumor progression of HCC. The pre-$S_2$ deletion region clusters at the N-terminus of the pre-$S_2$ region, predominantly in the range of 40 to 60 nucleotides long, although some cases contain deletions of as short as 10 nucleotides and still present type II GGH morphology (3). Some of the pre-$S_2$ mutant LHBS also harbors a point mutation at the pre-$S_2$ ATG start codon, causing no synthesis of the middle S antigen (FIG. 2). The region commonly deleted in the pre-$S_2$ mutant LHBS contains a CD8 T-cell epitope, which proposes a hypothesis that this type of mutant LHBS escapes from immune surveillance then becomes a selective clone in long-term persistence of HBV infection.

In the past 10 years or so, the inventors of the present invention focused on studying the pathological effects caused by the pre-S mutant LHBS, especially the pre-$S_2$ type, since this type of LHBS is particularly highly associated with HCC. It was found that the both of the pre-$S_1$ and -$S_2$ mutant LHBS distribute in endoplasmic reticulum (ER) of hepatocytes and induce ER stress (4). However, the pre-$S_2$ mutant LHBS specifically induces ER stress-induced growth proliferation mediated through the NFκB pathway (5). The pre-$S_2$ mutant LHBS also induces significantly higher level of ER stress-dependent oxidative stress and oxidative DNA damages than the wild-type or pre-$S_1$ mutant LHBS do, which leads to genomic instability and consequently hepatocellular carcinogenesis (6). In addition, the pre-$S_2$ mutant LHBS specifically induces cyclin A over-expression (7) and directly interacts with Jun activation domain-binding protein 1 (JAB1) to cause inactivation of the tumor suppressor retinoblastoma and cell cycle progression (8). Together these findings have offered clear lines of evidence of that the pre-$S_2$ mutant LHBS likely plays an important role in HBV-induced HCC.

The pre-$S_2$ mutant LHBS is relatively low at acute phase of HBV infection but greatly increased in the long-term period of HBV infection. In HCC, it is higher than 60%, which indicates that it is highly prevalent in late phase of chronic HBV infection and significantly associated with advanced liver diseases such as cirrhosis and HCC (9). To detect the pre-S deletion in LHBS, we previously developed a Pre-S Gene Chip, which detects the pre-S deletion based on DNA hybridization of the HBS genes in patients to the DNA probes on the chip. It was found that the WT and pre-S mutant LHBS often co-exist in one individual HBV carrier, which makes the detection of the pre-S mutant difficult. Moreover, it requires labor-intensive process for cloning and isolating each individual gene product before the chip analysis.

Furthermore, the pre-$S_2$ deletion mutants have also been shown to increase after anti-viral therapies using nucleoside analogs to chronic HBV carriers, suggesting that the carriers presenting the pre-$S_2$ mutant large HBV surface (LHBS) protein are the ones in high risk to HCC. See Zhang et al. BMC Microbiology, 12: 307-316 (2012). Thus, there is a need to develop a rapid and accurate method for detecting deletions in the HBV Pre-S region, thereby assessing a HBV carrier's risk of developing cirrhosis/HCC.

REFERENCES

1. Gerber M A, Hadziyannis S, Vernace S, Vissoulis C. Incidence and nature of cytoplasmic hepatitis B antigen in hepatocytes. Lab Invest. 1975; 32:251-256.

2. Fan Y F, Lu C C, Chang Y C, Chang T T, Lin P W, Lei H Y, Su I J. Identification of a pre-S2 mutant in hepatocytes expressing a novel marginal pattern of surface antigen in advanced disease of chronic hepatitis B virus infection. J. Gastroenterol. Hepatol. 2000; 15:519-528.
3. Fan Y F, Lu C C, Chen W C, et al. Prevalence and significance of hepatitis B virus (HBV) pre-S mutants in serum and liver at different replicative stages of chronic HBV infection. Hepatology 2001; 33:277-286.
4. Wang H C, Wu H C, Chen C F, et al. Different types of ground glass hepatocytes in chronic hepatitis B virus infection contain specific pre-S mutants that may induce endoplasmic reticulum stress. Am. J. Pathol. 2003; 163: 2441-2449.
5. Hung J H, Su I J, Lei H Y, et al. Endoplasmic reticulum stress stimulates the expression of cyclooxygenase-2 through activation of NF-kappaB and pp 38 mitogen-activated protein kinase. J Biol Chem. 2004; 279:46384-46392.
6. Hsieh Y H, Su I J, Wang H C, et al. The pre-S mutant surface antigens in chronic hepatitis B virus infection induce oxidative stress and DNA damage. Carcinogenesis 2004; 25:2023-2032.
7. Wang H C, Huang W, Lai M D, et al. Aberrant cyclin A expression and centrosome overduplication induced by hepatitis B virus pre-S2 mutants and its implication in hepatocarcinogenesis. Carcinogenesis 2012; 33:466-472.
8. Hsieh Y H, Su I J, Wang H C, et al. Hepatitis B virus pre-S2 mutant surface antigen induces degradation of cyclin-dependent kinase inhibitor p27Kip1 through c-Jun activation domain-binding protein 1. Mol Cancer Res 2007; 5:1063-1072.
9. Shen F C, Su I J, Wu H C, et al. A Pre-S Gene Chip to detect the pre-S deletions in the hepatitis B virus large surface antigen as a predictive marker for hepatoma risk in the chronic HBV carriers. J. Biomed. Sci. 2009; 16:84-91.
10. Shafritz D A, Shouval D, Sherman H I, et al. Integration of hepatitis B virus DNA into the genome of liver cells in chronic liver disease and hepatocellular carcinoma. Studies in percutaneous liver biopsies and post-mortem tissue specimens. N Engl J Med 1981; 305:1067-1073.
11. Guerrieri F, Belloni L, Pediconi N, Levrero M. Molecular mechanisms of HBV-associated hepatocarcinogenesis. Semin Liver Dis 2013; 33:147-156.
12. Hung L, Kumar V. Specific inhibition of gene expression and transactivation functions of hepatitis B virus X protein and c-myc by small interfering RNAs. FEBS Lett 2004; 560:210-214.
13. Becker S A, Lee T H, Butel J S, et al. Hepatitis B virus X protein interferes with cellular DNA repair. J Virol 1998; 72:266-272.
14. Chen B F, Liu C J, Jow G M, et al. High prevalence and mapping of pre-S deletion in hepatitis B virus carriers with progressive liver diseases. Gastroenterology 2006; 130:1153-1168.
15. Chen C H, Hung C H, Lee C M, et al. Pre-S deletion and complex mutations of hepatitis B virus related to advanced liver disease in HBeAg-negative patients. Gastroenterology 2007; 133:1466-1474.
16. Tsai H W, Lin Y J, Lin P W, et al. A clustered ground-glass hepatocyte pattern represents a new prognostic marker for the recurrence of hepatocellular carcinoma after surgery. Cancer 2011; 117:2951-2960.
17. Zhang D, Dong P, Zhang K, et al. Whole genome HBV deletion profiles and the accumulation of preS deletion mutant during antiviral treatment. BMC Microbiol. 2012; 12:307.

SUMMARY OF THE INVENTION

Therefore, it is a primary objective of the present invention to provide a HBS-specific antibody, a LHBS-specific antibody, a wild type (WT) LHBS-specific antibody, an immunoassay kit comprising the antibodies, and a method of detecting pre-$S_2$ deletion mutant LHBS using the immunoassay kit to evaluate the pre-$S_2$ mutant LHBS as a potential high-risk marker for HCC incidence in chronic HBV carriers and recurrence in HCC patients after hepatectomy surgery.

To achieve the foregoing objective, the present invention provides a large hepatitis B virus surface protein (LHBS)-specific antibody, specifically binding to a recombinant protein shown as the amino acid sequence of SEQ ID NO: 1.

Preferably, the LHBS antibody may be produced by the hybridoma cell line deposited on Sep. 1, 2014 under accession number BCRC960490 at the Food Industry Research and Development Institute, 331 Shih-Pin Road, Hsinchu 300, Taiwan, and also on Oct. 31, 2014 under accession number DSM ACC3253 at Leibniz-Institut DSMZ-Deutsche Sammlung von Mikroorganismen und Zellkulturen GmbH (DSMZ), Inhoffenstr. 7B, 38124 Braunschweig, Germany.

Preferably, the hybridoma cell line may be fused by myeloma cells and splenocyte of mice immunized with the recombinant protein shown as the amino acid sequence of SEQ ID NO: 1.

Preferably, the antibody may be an antigen-binding fragment or a functional variant of the LHBS-specific antibody, and the functional variant comprises the same complementary determining regions (CDRs) as the LHBS-specific antibody.

To achieve the foregoing objective, the present invention provides a wild type large hepatitis B virus surface protein (WT LHBS)-specific antibody, specifically binding to a peptide shown as the amino acid sequences of SEQ ID NO: 2.

Preferably, the WT LHBS antibody may be produced by the hybridoma cell line deposited on Jul. 16, 2014 under accession number BCRC960488 at the Food Industry Research and Development Institute, 331 Shih-Pin Road, Hsinchu 300, Taiwan, and also on Oct. 31, 2014 under accession number DSM ACC3251 at Leibniz-Institut DSMZ-Deutsche Sammlung von Mikroorganismen und Zellkulturen GmbH (DSMZ), Inhoffenstr. 7B, 38124 Braunschweig, Germany.

Preferably, the hybridoma cell line may be fused by myeloma cells and splenocyte of mice immunized with the peptide shown as the amino acid sequences of SEQ ID NO: 2.

Preferably, the antibody may be an antigen-binding fragment or a functional variant of the WT LHBS-specific antibody, and the functional variant comprises the same complementary determining regions (CDRs) as the WT LHBS-specific antibody.

To achieve the foregoing objective, the present invention provides a hepatitis B virus surface protein (HBS)-specific antibody, specifically binding to a peptide shown as the amino acid sequences of SEQ ID NO: 3.

Preferably, the HBS antibody may be produced by the hybridoma cell line deposited on Oct. 22, 2014 under accession number BCRC960491 at the Food Industry Research and Development Institute, 331 Shih-Pin Road, Hsinchu 300, Taiwan, and also on Oct. 31, 2014 under accession number DSM ACC3252 at Leibniz-Institut DSMZ-Deutsche Sammlung von Mikroorganismen und Zellkulturen GmbH (DSMZ), Inhoffenstr. 7B, 38124 Braunschweig, Germany.

Preferably, the hybridoma cell line may be fused by myeloma cells and splenocyte of mice immunized with the peptide shown as the amino acid sequences of SEQ ID NO: 3.

Preferably, the antibody may be an antigen-binding fragment or a functional variant of the HBS-specific antibody, and the functional variant comprises the same complementary determining regions (CDRs) as the HBS-specific antibody.

Preferably, the antigen-binding fragment may be a Fab or F(ab')$_2$ fragment.

Preferably, a signal generating unit may further be conjugated to the antibody.

Preferably, the signal generating unit may comprise a radioactive marker, a fluorescent marker, a phosphorescent marker, a chemiluminescent marker or a labeling enzyme.

Preferably, the labeling enzyme may comprise a horse radish peroxidase or an alkaline phosphatase.

To achieve the foregoing objective, the present invention further provides an immunoassay kit for detecting LHBS and WT LHBS in a biological sample, comprising: a substrate; a first antibody immobilized on the substrate, and the first antibody specifically binding to amino acid residues 1-226 of hepatitis B virus surface protein; a blocking solution for blocking a unconjugated portion; a second antibody specifically binding to amino acid residues 1-119 of large hepatitis B virus surface protein and a third antibody specifically binding to amino acid residues 125-142 of large hepatitis B virus surface protein; and a reaction substrate for reacting with the signal generating unit conjugated to the second and the third antibodies.

Preferably, the first antibody may be a hepatitis B virus surface protein-specific antibody produced by a hybridoma cell line deposited on Oct. 22, 2014 under accession number BCRC960491 at the Food Industry Research and Development Institute, 331 Shih-Pin Road, Hsinchu 300, Taiwan, and also on Oct. 31, 2014 under accession number DSM ACC3252 at Leibniz-Institut DSMZ-Deutsche Sammlung von Mikroorganismen und Zellkulturen GmbH (DSMZ), Inhoffenstr. 7B, 38124 Braunschweig, Germany, or progeny thereof.

Preferably, the second antibody may be a large hepatitis B virus surface protein-specific antibody produced by a hybridoma cell line deposited on Sep. 1, 2014 under accession number BCRC960490 at the Food Industry Research and Development Institute, 331 Shih-Pin Road, Hsinchu 300, Taiwan, and also on Oct. 31, 2014 under accession number DSM ACC3253 at Leibniz-Institut DSMZ-Deutsche Sammlung von Mikroorganismen und Zellkulturen GmbH (DSMZ), Inhoffenstr. 7B, 38124 Braunschweig, Germany, or progeny thereof.

Preferably, the third antibody may be a wild type large hepatitis B virus surface protein-specific antibody produced by a hybridoma cell line deposited on Jul. 16, 2014 under accession number BCRC960488 at the Food Industry Research and Development Institute, 331 Shih-Pin Road, Hsinchu 300, Taiwan, and also on Oct. 31, 2014 under accession number DSM ACC3251 at Leibniz-Institut DSMZ-Deutsche Sammlung von Mikroorganismen und Zellkulturen GmbH (DSMZ), Inhoffenstr. 7B, 38124 Braunschweig, Germany, or progeny thereof.

Preferably, the blocking solution may comprise skim milk, bovine serum albumin, or casein.

Preferably, the immunoassay kit may further comprise a wash solution, and the wash solution comprises PBS, TBS, PBS including a detergent, or TBS including a detergent.

Preferably, the reaction substrate may be tetramethylbenzidine (TMB) if the signal generating unit may be a horse radish peroxidase.

To achieve the foregoing objective, the present invention further provides a method of detecting a pre-S$_2$ deletion mutant large hepatitis B virus surface protein in a biological sample, comprising: incubating a biological sample with a first antibody immobilized on a substrate to bind a hepatitis B virus surface protein to the first antibody, wherein the first antibody specifically binds to amino acid residues 1-226 of hepatitis B virus surface protein; detecting a large hepatitis B virus surface protein and a wild type large hepatitis B virus surface protein bound to the immobilized first antibody by incubating the bound hepatitis B virus surface protein with a second antibody specifically binding to amino acid residues 1-119 of large hepatitis B virus surface protein and a third antibody specifically binding to amino acid residues 125-142 of large hepatitis B virus surface protein, respectively; and calculating the amount of the pre-S$_2$ deletion mutant large hepatitis B virus surface protein by subtracting the amount of the wild type large hepatitis B virus surface protein from that of the large hepatitis B virus surface protein.

Preferably, the biological sample may be isolated from a human.

Preferably, the human may be a HBV carrier or a liver cancer patient.

Preferably, the HBV carrier may be HBeAg-negative, with HBV viral load higher than $10^4$ copies/ml of the biological sample, or the combination thereof.

Preferably, the method may further comprise a step of assessing a risk of developing hepatocellular carcinoma or cirrhosis of the HBV carrier.

Preferably, the HBV carrier may have undergone an antiviral therapy using nucleoside analogs or interferon drugs.

Preferably, the method may further comprise a step of assessing a risk of developing hepatocellular carcinoma or cirrhosis after the antiviral therapy.

Preferably, the liver cancer patient may be a hepatocellular carcinoma patient undergone a hepatectomy surgery.

Preferably, the method may further comprise a step of assessing risk of cancer recurrence of the hepatocellular carcinoma patient at 1 to 12 month(s) after the surgery.

Preferably, the biological sample may be whole blood, plasma or serum.

Preferably, the method may further comprise a step of isolating hepatitis B virus surface protein from the biological sample.

The HBS-specific antibody, the LHBS-specific antibody, the WT LHBS-specific antibody, an immunoassay kit comprising the antibodies, and the method of detecting pre-S$_2$ deletion mutant LHBS using the immunoassay kit according to embodiments of the present invention may have the following advantages:

(1) The immunoassay kit comprising the antibodies and the method of detecting pre-S$_2$ deletion mutant LHBS using the same of the present invention may be easy to calculate the amount of the pre-S$_2$ deletion mutant LHBS in a biological sample without mutual influence between the wild-type and pre-S mutant LHBS.

(2) The immunoassay kit comprising the antibodies and the method of detecting pre-S$_2$ deletion mutant LHBS using the same of the present invention may reduce the labor-intensive process for cloning and isolating each individual gene product before analysis comparing to Pre-S Gene Chip analysis.

BRIEF DESCRIPTION OF THE DRAWINGS

The properties and effects of the present invention will now be described in more details hereinafter with reference to the accompanying drawings that show various embodiments of the invention as follows.

DETAILED DESCRIPTION OF THE PREFERRED EMBODIMENTS

The technical content of the present invention will become apparent by the detailed description of the following embodiments and the illustration of related drawings as follows.

DEFINITIONS

The term "HBS" as used herein refers to surface protein of hepatitis B virus (HBV). The HBS comprises large HBS, middle HBS and small HBS, which are different splicing forms of the surface protein.

The term "LHBS" as used herein refers to large surface protein comprising pre-S$_1$, pre-S$_2$ and S regions.

The term "WT LHBS" as used herein refers to wild-type large surface protein comprising pre-S$_1$, pre-S$_2$ and S regions with a length of 401 amino acids.

The term "pre-S$_2$ deletion mutant LHBS" as used herein refers to large surface protein with a deletion around 20 amino acids in the pre-S$_2$ region.

The term "detecting" is used in the broadest sense to include both qualitative and quantitative measurements of a target molecule. In one aspect, the detecting method as described herein is used to identify the mere presence of HBS, LHBS or WT LHBS in a biological sample. In another aspect, the method is used to test whether HBS, LHBS or WT LHBS in a sample is at a detectable level. In yet another aspect, the method can be used to quantify the amount of HBS, LHBS or WT LHBS in a sample and further to compare the HBS, LHBS or WT LHBS levels from different samples The term "biological sample" refers to a body sample from any animal, but preferably is from a mammal, more preferably from a human. Most preferably, such biological sample is from HBV carrier or a liver cancer patient. Such samples include biological fluids such as serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, and cellular extracts, in which HBS may be detected. The preferred biological sample herein is serum, plasma or whole blood.

The term "first antibody" refers to an antibody capable of binding and capturing a target molecule, HBS, in a sample such that under suitable condition, the first antibody-HBS complex can be separated from the rest of the sample. Typically, the first antibody is immobilized or immobilizable. In a sandwich immunoassay, the first antibody is preferably an antibody, antigen-binding fragment, a functional variant or a mixture thereof against a HBS.

The terms "second antibody" and "third antibody" refer to an antibody that is capable of being detected either directly through labeling a signal generating unit, or indirectly through, e.g., another antibody that is labeled with the signal generating unit. The preferred second antibody and third antibody are LHBS-specific antibody and WT LHBS-specific antibody, respectively.

The term "signal generating unit" refers to a moiety or technique used to detect the presence of the second antibody and the third antibody in the immunoassay herein and includes detection agents that amplify the immobilized label such as label captured onto a microtiter plate. Preferably, the signal generating unit is a radioactive marker, a fluorescent marker, a phosphorescent marker, a chemiluminescent marker or a labeling enzyme. More preferably, the signal generating unit is the labeling enzyme comprising horse radish peroxidase or alkaline phosphatase.

The term "antibody" is used in the broadest sense and includes monoclonal antibodies (including agonist, antagonist, and neutralizing antibodies), polyclonal antibodies, multivalent antibodies, multispecific antibodies, and antibody fragments so long as they exhibit the desired binding specificity.

Material and Methods

Development of Monoclonal Antibodies that Specifically Recognize LHBS and WT LHBS To generate monoclonal antibodies specifically recognizing LHBS, briefly, inventors purified the recombinant pre-S region protein (SEQ ID NO: 1) from *E. coli* and i.p. injected it into BALB/C mice to generate monoclonal antibodies. The activated splenocytes were fused with melanoma cells to generate hybridomas. The hybridoma clones which showed the highest affinities to the pre-$S_1$ region protein among all were i.p. injected into mice for ascites production to amplify the antibodies. The antibody clones which showed the highest affinity to LHBS among all were further selected for further investigation. Preferably, the LHBS antibody may be produced by the hybridoma cell line deposited on Sep. 1, 2014 under accession number BCRC960490 at the Food Industry Research and Development Institute, 331 Shih-Pin Road, Hsinchu 300, Taiwan, and also on Oct. 31, 2014 under accession number DSM ACC3253 at Leibniz-Institut DSMZ-Deutsche Sammlung von Mikroorganismen und Zellkulturen GmbH (DSMZ), Inhoffenstr. 7B, 38124 Braunschweig, Germany.

To generate the monoclonal antibodies specifically recognizing the WT LHBS, the amino acid sequence (SEQ ID NO: 2) of the protein region that is deleted in the pre-$S_2$ deletion mutant LHBS has been synthesized into a peptide and injected to mice for generating the WT LHBS-specific antibody. The mouse whose serum showed the highest affinities to the wild-type LHBS was selected for further investigation. Preferably, the WT LHBS antibody may be produced by the hybridoma cell line deposited on Jul. 16, 2014 under accession number BCRC960488 at the Food Industry Research and Development Institute, 331 Shih-Pin Road, Hsinchu 300, Taiwan, and also on Oct. 31, 2014 under accession number DSM ACC3251 at Leibniz-Institut DSMZ-Deutsche Sammlung von Mikroorganismen und Zellkulturen GmbH (DSMZ), Inhoffenstr. 7B, 38124 Braunschweig, Germany. The detail embodiments are described below.

Antigen Preparation for Mouse Immunization

Preparation for *E. coli* Cell Lysates

Recombinant protein, pre-$S_1$, protein sequence consulted from NCBI (National Center for Biotechnology Information), and hepatitis B virus serotype, adw2, were adapted for cloning template reference. Pre-$S_1$ region (a.a. 1-119, SEQ ID NO: 1) of LHBS was expressed by *E. coli* protein expression system with Rosetta strain. The pre-$S_1$ recombinant plasmid in *E. coli* cells was adapted from lab stock that pre-$S_1$ segment was designed to be cloned into plasmid, pET21c, with 6×-His tag genes at the 5' end of pre-$S_1$ gene. By transforming this plasmid into Rosetta cells, then colonies were picked and culture with LB medium, 37° C., until the $OD_{600}$ reach 0.6-0.8 around 16 hours; and refresh the culture in new batch of LB medium (pH 8) and incubate in 37° C. when $OD_{600}$ read 0.8~1.0; 100 mM IPTG is added to 0.2 mM final concentration for 6 hours induction in 25° C. Induction sample was then harvested by 6000 rpm, 10 minutes centrifugation, the supernatant was removed, and the pellet was collected for sonication to acquire cell lysates. The collected cell pellet was resuspended in 1× binding buffer (20 mM phosphate solution, pH 7.4, 0.5 M NaCl, and 20 mM Imidazole), and by sonication in 130 watt, 20 kHz, 75% amplified burst for 30 seconds every time and for 3-4 times. Followed by 10000 rpm, 30 minutes centrifugation in 4° C. to discard the cell debris, the supernatant of cell lysates was acquired for $Ni^{2+}$-NTA chromatography purification.

Protein Purification by $Ni^{2+}$-Chelating Chromatography

Pre-$S_1$ recombinant protein purification was processed with packing $Ni^{2+}$ resin first by adding 2 resin volumes of 100 mM $Ni^{2+}$ (100 mM $NiSO_4$) with proper volume of chelating resin. The column was then washed with 5 resin volumes of MiniQ water, and conditioned with 5 resin volumes of binding buffer. Then, the *E. coli* cell lysates were added to the $Ni^{2+}$ column and then washed with washing buffer 1 (60 mM Immidazole, 20 mM sodium phosphate, 0.5 M sodium chloride, pH 7.4), washing buffer 2 (80 mM Immidazole, 20 mM sodium phosphate, 0.5 M sodium chloride, pH 7.4), with each 10 resin volumes. Finally, eluted the target protein with 3 resin volume of elution buffer (500 mM Immidazole, 20 mM sodium phosphate, 0.5 M sodium chloride, pH 7.4), and then check protein purification quality and efficiency by SDS-PAGE electrophoresis and immunoblotting on collected sample from each step. The pre-$S_1$ recombinant protein was further purified by DEDE-ion exchange column to reach the criteria for mouse immunization.

Pre-$S_1$ Region Monoclonal Antibody (LHBS-Specific Antibody) Production

The pre-$S_1$ region recombinant protein, acquired from *E. coli* system, 0.5 mg/ml, total around 3 mg was sent for commercial antibody production. The mouse immunization and hybridoma production were processed by Protech, Inc., Taiwan. Mice antisera can be acquired after 2.5 months for antigen specific antibody titering to select an ideal mouse for sacrifice and hybridoma fusion experiment. Later, culture medium from hybridoma can be also acquired for antigen specific antibody titering several times to select the perfect clones for antigen specific monoclonal antibody production. The hybridoma cells were then acquired and isotyped to ensure these cells are monoclonal or yet and limit dilution required to get cells with monoclonal antibodies.

Immunized Mouse Serum Titering

Enzyme-Linked Immunosorbent Assay (ELISA)

Antibody titering antigens were diluted with 1× phosphate-buffered saline (PBS) to 20 ng/μl and applied to 96-well with 50 μl (1 μg) each well, and antigen coated in 4° C. for overnight (12-16 hours). On the following day that each well was washed 2 times with PBST (1× PBS, 0.1% Tween-20) 200 μl each, and blocked with 100 μl 1% Bovine serum albumin (BSA) for 2 hours in room temperature (about 25° C.). Then the wells were washed by PBST 2 times with 200 μl each, and then the serial dilutions by 10 folds of test sera/antibodies were added, incubated in 37° C. for 2 hours. After 2 hours incubation of antisera/antibodies with antigens, the 96-well plate was then washed by 200 μl PBST each well for 4 times, and ensured to completely discard the solution from wells, then secondary antibodies conjugated with horseradish phosphatase (HRP) were added to detect the bound primary antibodies. The secondary antibody was used depend on the species of primary antibody; usually were anti-mouse IgG, or anti-rabbit IgG secondary antibodies. Secondary antibodies were 1:5000 diluted in PBST and 50 μl for each well, and incubated in 37° C. for 30 minutes. After incubation, the 96-well plate was washed by PBST for 4 times, and added with TMB, substrate for HRP, 50 μl for each and wait for visible color reaction and stop the reaction by another 50 μl 2N $H_2SO_4$, then detect the OD values under 450 nm to calculate and plot the curve for antibody specificity.

Selection of Antigen Specific Antibody Producing Hybridoma

Hybridoma culture media were acquired from Protech Inc., Taiwan, after 1.5-2 months, and by ELISA to check antigen specific titers and select for positive clones. The 96-well plate was coated with antigens, pre-$S_1$ region protein that were used for immunization, WT LHBS (pre-$S_1$+ pre-$S_2$ region) recombinant protein, pre-$S_2$ mutant (pre-$S_1$+ pre-$S_2$ deletion mutant region) recombinant protein, and His-tagged *E. coli* recombinant human macrophage migration inhibitory factor (hMIF), used to rule out his tag specificity. Antigen coated was 1 µg for each well and proteins were diluted in PBS for 20 ng/µl and 50 ul for each well. Then these hybridoma culture media were added as primary antibody, 100 µl for each well, and incubated under 37° C. for 2 hours. The following steps are the same as above ELISA protocol for mouse antiserum titering.

Validation and Amplification of the Monoclonal Antibodies for the LHBS and the WT LHBS The monoclonal antibodies for the LHBS and the WT LHBS were further amplified and characterized for their properties. Their sensitivities and specificities in the following experiments were evaluated by ELISA. In addition, to use these antibodies to develop a high-sensitive immunoassay kit, the purified LHBS and WT LHBS antibodies were also directly conjugated with hydrogen peroxidase (HRP) for colorimetry detection. The brief protocol for antibody conjugation to HRP is: Mixing 2 mg of peroxidase and 100 uL of freshly prepared 0.1 M sodium periodate and stir the solution for 20 min at room temperature in the dark. Dialyze the modified enzyme against 1 mM sodium acetate buffer (pH 4.4) overnight at 4° C. Dissolve 4 mg of IgG in 500 uL of 10 mM sodium carbonate buffer (pH 9.5), and then adjust the pH of the dialyzed enzyme solution to 9.5 by using sodium borohydride solution. Stir the mixture by gel filtration on a column of Sepharose CL-6B in PBS. Determine the $A_{280}$ and $A_{403}$. Pool the fractions in the first peak (both $A_{280}$ and $A_{403}$ peaks coincide). Finally, add BSA to give a final concentration of 5 mg/mL, and store the conjugate in aliquots at −20° C.

A lysis solution was prepared and used to release the HBV surface antigens from HBV viral particle in the serum. The lysis solution were composed of 2% HP-beta-CD (hydroxypropyl-beta-cyclodextrin), 0.5% Triton X-114, 0.5% Tween-20, 2 mM DTT (Dithiothreitol), and 1% 2-Mercaptoethanol, all dissolved in 20 mM HEPES, pH 7. The sandwich ELISA was processed with anti-HBS polyclonal antibodies coated onto 96-well plate by 2 µg/ml and 50 µl each well as capture antibody. After 4° C. overnight antibody coating step, the 96-well plate was then washed with PBST (0.1% Tween-20 in phosphate buffered saline) 200 µl each well for 2 times and blocked with 1% BSA for 2-3 hours in room temperature (~25° C.). With 1% BSA (Bovine serum albumin), the antibodies with non-specific activities can be blocked by serum proteins. The blocking step was then stopped and washed with PBST for 2-3 times for extra serum proteins to be removed.

Serum samples were 100-fold diluted in phosphate-buffered saline (PBS), and added into the 96-well with anti-HBS antibodies coated for 50 µl each. Then LHBS-specific and WT LHBS-specific monoclonal antibodies worked as detection antibody were 1:5000 diluted in previous mentioned lysis solution and added into each well with diluted serum by 50 µl. The LHBS and WT LHBS detection reaction was then incubated for 2 hours in 37° C. The 96-well plate was later washed with 200 µl PBST (0.1% Tween-20 in PBS) each well for 5 times and 1:5000 PBS diluted HRP-conjugated anti-mouse IgG antibodies were then added by 50 µl into each reaction well as secondary antibody and incubate in 37° C. for another 1 hour. Finally, the reaction plate was washed with 200 µl PBST each well for 5 times and 50 µl HRP (Horseradish peroxidase) substrate, TMB, was added for visible color reaction with 37° C. incubation for 5-10 minutes. And the OD values were detected by 450 nm on ELISA reader.

Figure 7:
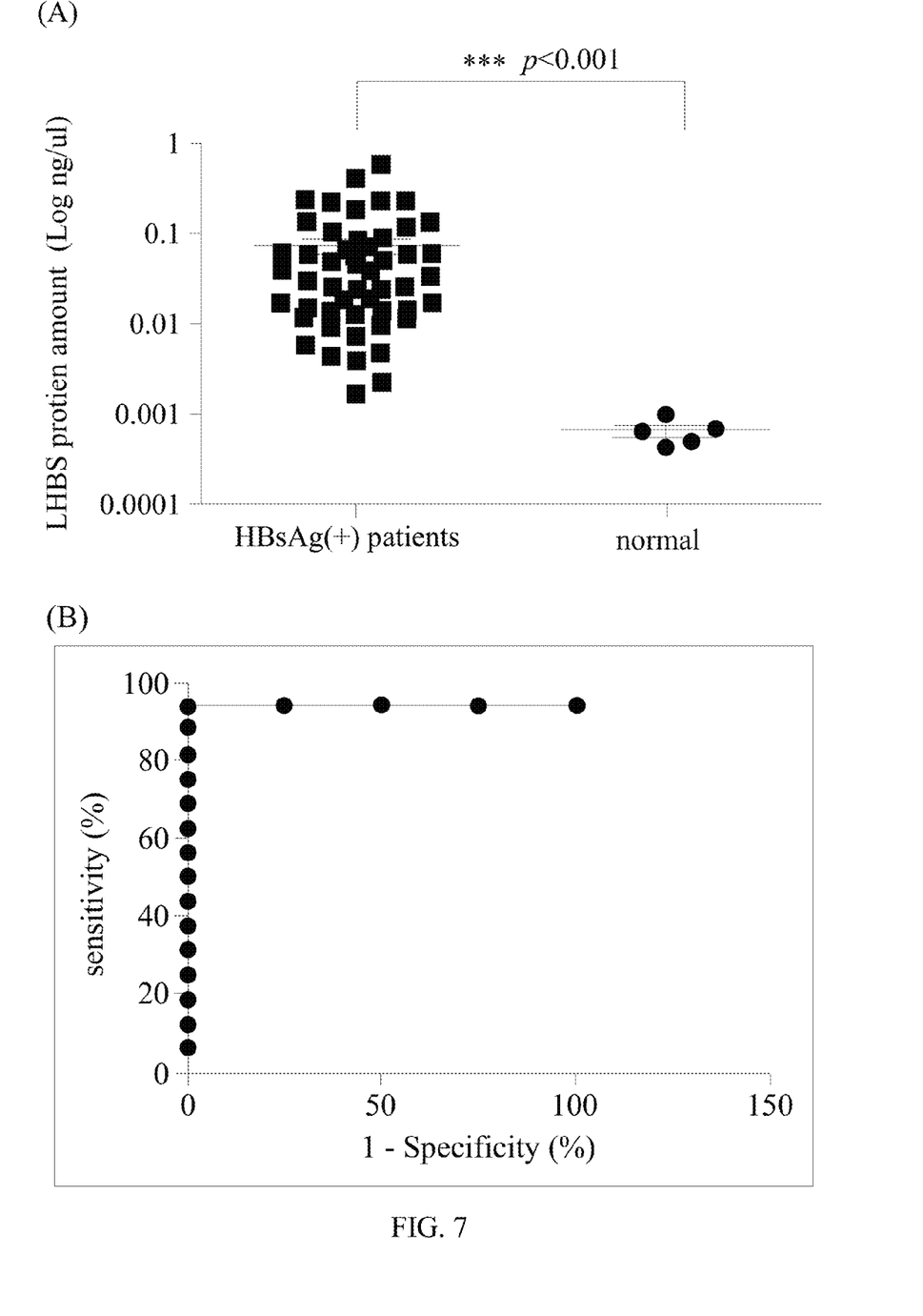
FIG. 7 is a schematic view of detection of LHBS in HBsAg(+) and HBsAg(−) patient sera. (A) The LHBS levels (ng/μl). (B) The ROC curve of the immunoassay kit according to embodiments of the present invention.

Development of an Immunoassay Kit to Detect the WT and Pre-$S_2$ Deletion Mutant LHBS in Serum Following purification and conjugation of the LHBS and the WT LHBS-specific monoclonal antibodies, these antibodies were used to develop an immunoassay kit. Sera of 50 HBV carriers were recruited and used as positive control. Concentrations of the LHBS and the WT LHBS in sera were determined by using the recombinant *E. coli* pre-S region WT and pre-$S_2$ deletion mutant proteins as the standards. The schematic representation of the ELISA system is shown in FIG. 7. The levels of HRP conjugated to the LHBS- and WT LHBS-specific antibodies represent those of the LHBS and the WT LHBS, respectively. Therefore, the subtracted value of the LHBS by the WT LHBS in the same serum specimen was the level of the pre-$S_2$ deletion mutant in it.

Results

Figure 4:
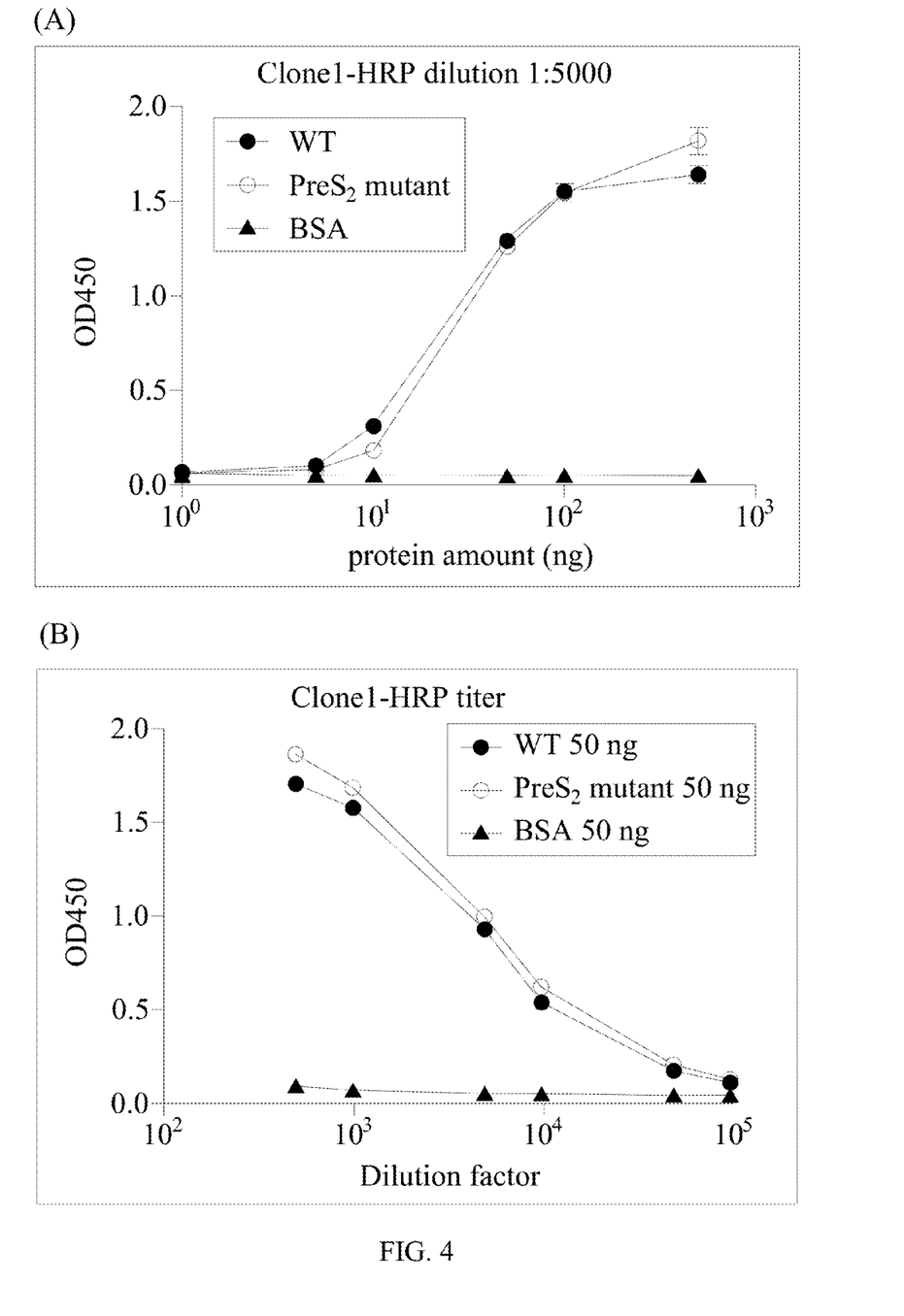
FIG. 4 demonstrates sensitivities and specificities of the LHBS antibody, detected by ELISA, according to embodiments of the present invention. (A) Binding of the LHBS antibody to various concentrations of the WT and pre-S$_2$ deletion mutant LHBS; and (B) Binding of various titrations of the LHBS antibody to the WT and pre-S$_2$ deletion mutant LHBS in the amounts of 50 ng.

In the embodiment, the protein comprising the amino acids shown in SEQ ID NO: 1 is expressed in *E. coli* as recombinant protein, purified to homogeneity then injected into mice for antibody generation. After several times of antibody boosting using the pre-$S_1$ region protein of SEQ ID NO: 1, the mouse spleens were removed. The homogenized splenocytes were fused with myeloma cells to generate hybridomas, which secrete the anti-LHBS monoclonal antibodies. Hybridoma cells that express high antibody titers are ip injected into mice for generation of ascites, where large amounts of antibodies exist. The monoclonal antibodies are purified from ascites, conjugated with horse radish peroxidase. The purified antibodies were employed to bind to the *E. coli* recombinant LHBS pre-$S_1$ region protein by ELISA assays. Monoclonal antibodies for the LHBS, the WT LHBS and the total HBS (including LHBS, MHBS and major HBS) have been developed. The results in FIG. 4 showed that the LHBS antibody recognizes both the WT and pre-$S_2$ deletion mutant LHBS equally well with the sensitivity of 10 ng protein (FIG. 4, part A) and the antibody remains binding affinity to the LHBS up to $5 \times 10^4$ dilution (FIG. 4, part B). This antibody was large-scale amplified, purified and conjugated with HRP for further immunoassay use.

Figure 5:
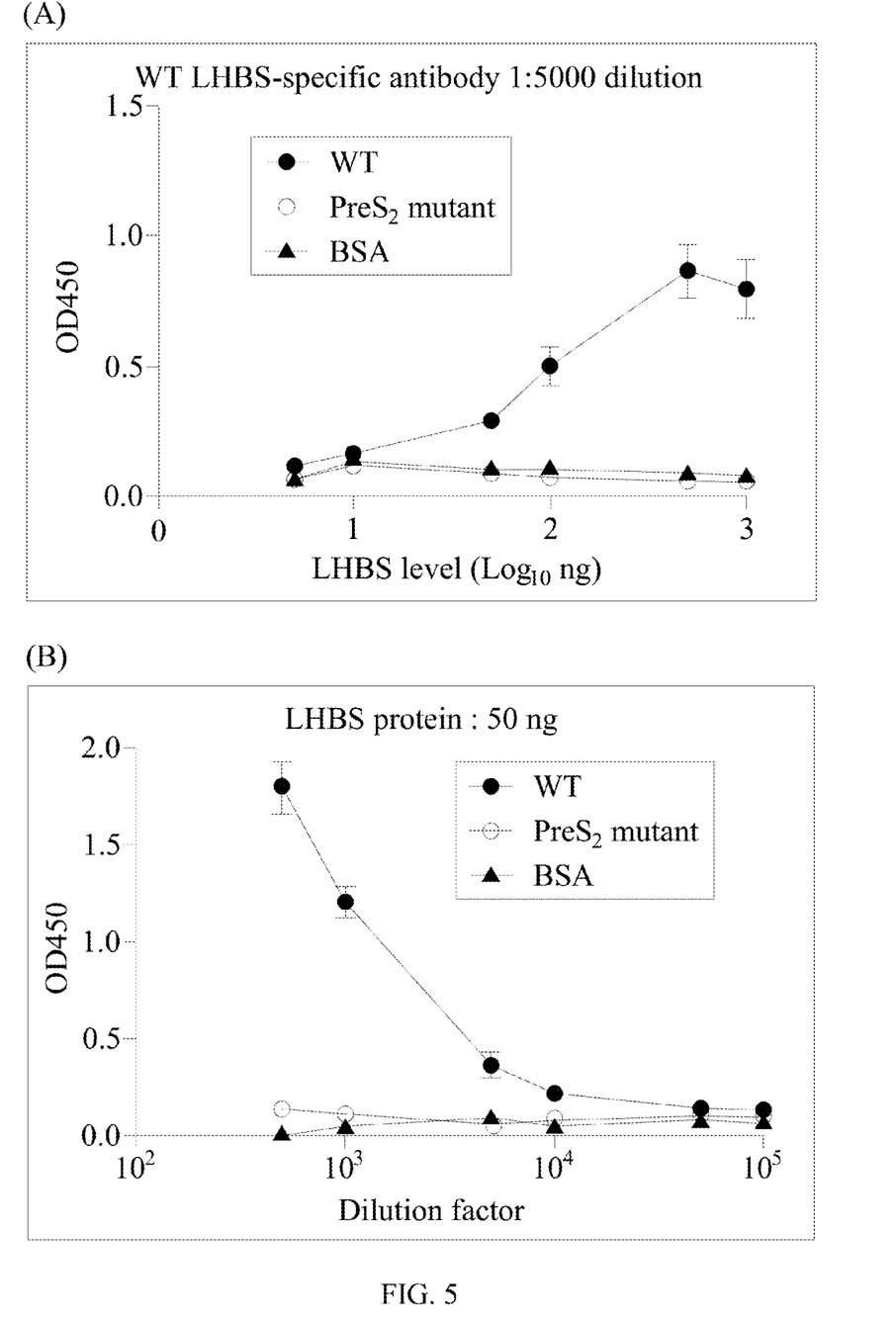
FIG. 5 demonstrates sensitivities and specificities of the WT LHBS-specific antibody, detected by ELISA, according to embodiments of the present invention. (A) Binding of the WT LHBS-specific antibody to various concentrations of the WT and pre-S$_2$ deletion mutant LHBS; and (B) Binding of various titrations of the WT LHBS-specific antibody to the WT and pre-S$_2$ deletion mutant LHBS in the amounts of 50 ng.

As for the WT LHBS-specific antibodies, the development processes is similar to that of LHBS-specific antibody except the antigen being the polypeptide of SEQ ID NO: 2, which will not further described here. The results in FIG. 5 showed that the WT LHBS antibody specifically recognizes the WT LHBS but not the pre-$S_2$ deletion mutant LHBS. Its binding sensitivity to the WT LHBS was approximate 30 ng (FIG. 5, part A) and the antibody remains binding affinity to the LHBS up to $10^4$ dilution (FIG. 5, part B). This antibody has been large-scale amplified, purified and conjugated with HRP for ELISA use.

Figure 3:
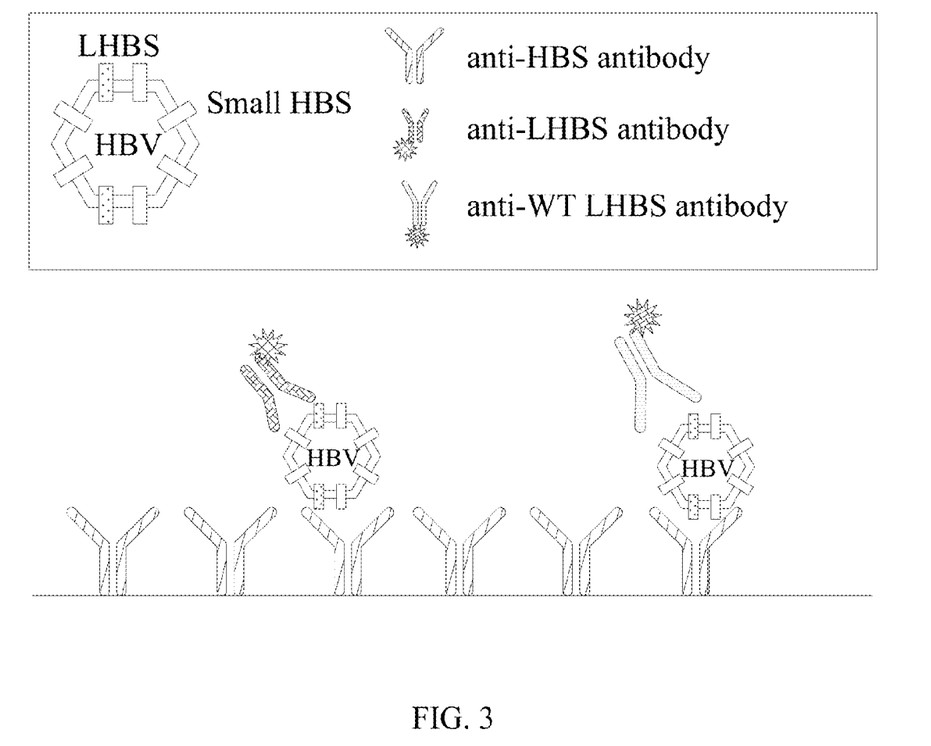
FIG. 3 is a schematic view of detecting LHBS and WT LHBS using the immunoassay kit according to embodiments of the present invention.
Figure 6:
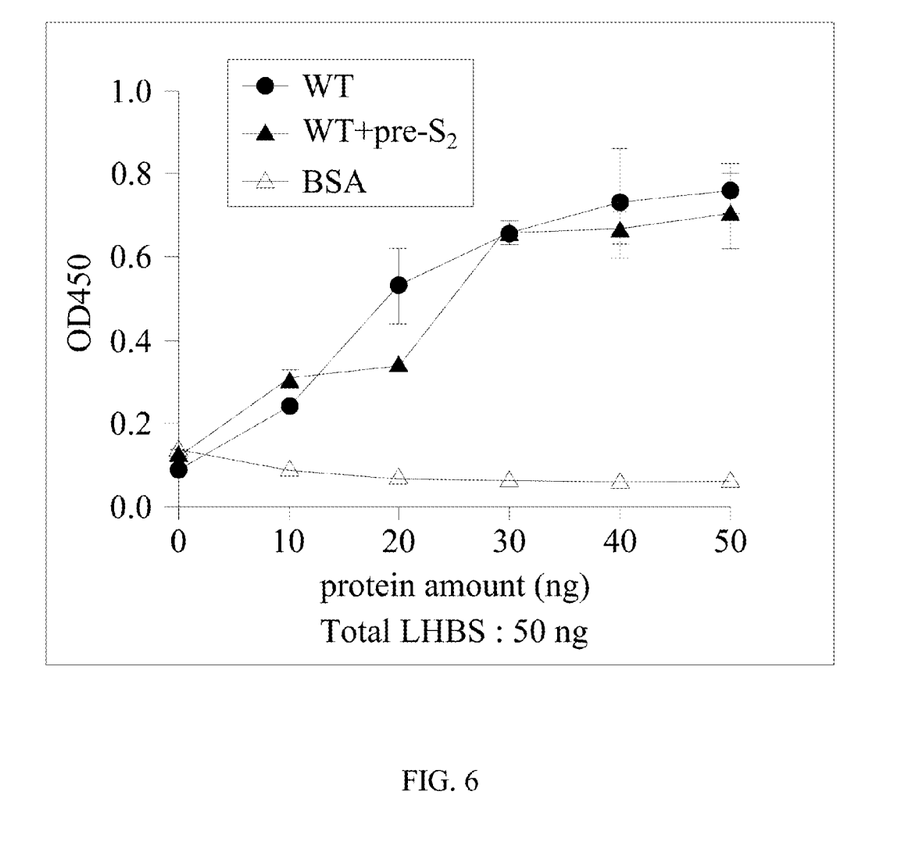
FIG. 6 is a schematic view of using the WT LHBS-specific antibody according to embodiments of the present invention to detect the LHBS and the WT LHBS. ●: WT only. ▲: WT/pre-S$_2$ deletion mutant LHBS mixed in various relative ratios. The LHBS amount is 50 ng.

The monoclonal antibodies generated in the embodiments were employed to construct a sandwich ELISA system to detect the LHBS and WT LHBS proteins (FIG. 3). Using this assay kit, the binding specificity of the WT LHBS-specific antibody to the WT LHBS protein was detected in the WT/pre-$S_2$ deletion mutant LHBS mix. The results in FIG. 6 show that the presence of the pre-$S_2$ deletion mutant does not appear to interfere the binding of the WT LHBS-specific antibody to the WT LHBS protein, indicating that this ELISA system can detect the two LHBS types with high specificity.

The sandwich ELISA system developed in this study was used to detect the LHBS levels in sera of HBV carriers. Fifty HBsAg$^{(+)}$ and 5 HBsAg$^{(-)}$ sera, previously detected using the Abbott HBsAg detection system, were investigated. The results found that all the HBsAg$^{(+)}$ cases showed significantly higher levels of LHBS than the HBsAg$^{(-)}$ cases (FIG.

7, part A). Analysis of the receiver operating characteristic (ROC) curve showed that setting up the cut-off value of 0.02 ng LHBS/μl serum could distinguish the positive and negative cases with high sensitivity and specificity (FIG. 7, part B). As for the detection of the pre-S$_2$ deletion mutant LHBS, the signals detected in the LHBS and the WT LHBS as the respective amounts of proteins, are used to calculate the amounts of the pre-S$_2$ deletion mutant LHBS, which is detectable by the LHBS-specific but not the WT LHBS-specific antibodies (Table 1). Through this calculation, the amount of pre-S$_2$ deletion mutant LHBS was obtained.

deletion mutant LHBS is a high-risk marker for HCC in chronic HBV carriers, as well as one for a poor prognosis in patients with HCC.

In this study, we developed a sandwich ELISA system to detect the pre-S$_2$ deletion mutant LHBS in sera. We previously developed a Pre-S Gene Chip, which detected the pre-S deletion based on DNA hybridization of the HBS genes in patients to the DNA probes on the chip (9). However, due to that the wild-type and pre-S mutant LHBS often co-exist in one individual HBV carrier, it often required the process of isolating individual HBS clones to

TABLE 1

Representative results of the ELISA detection for the wild type and pre-S$_2$ mutant LHBS in human sera of HBV carriers.

| | LHBS | | | | Wild type LHBS | | | | Pre-S2 mutant amount (ng) |
|---|---|---|---|---|---|---|---|---|---|
| Serum sample | OD*1 | OD*2 | Average OD* | Protein amount (ng) | OD*1 | OD*2 | Average OD* | Protein amount (ng) | |
| 1 | 0.21 | 0.23 | 0.22 | 0.39 | 0.27 | 0.32 | 0.29 | 0.40 | 0 |
| 2 | 1.17 | 1.14 | 1.16 | 2.70 | 0.45 | 0.52 | 0.49 | 0.99 | 1.71 |
| 3 | 0.32 | 0.32 | 0.32 | 0.63 | 0.09 | 0.07 | 0.08 | 0.01 | 0.62 |
| 4 | 0.71 | 0.70 | 0.70 | 1.59 | 0.14 | 0.14 | 0.14 | 0.13 | 1.46 |
| 5 | 0.37 | 0.37 | 0.37 | 0.75 | 0.11 | 0.11 | 0.11 | 0.06 | 0.69 |
| 6 | 0.25 | 0.25 | 0.25 | 0.45 | 0.18 | 0.19 | 0.19 | 0.24 | 0.21 |
| Non-carrier | 0.07 | 0.06 | 0.06 | 0 | 0.05 | 0.04 | 0.04 | 0 | 0 |

*OD: optical density of light absorbance, which is generated by the ELISA reaction products.

Discussion

Hepatocellular carcinoma caused by chronic hepatitis B virus (HBV) infection is the most frequent visceral neoplasm worldwide. The virus infection induces HCC through multiple pro-carcinogenic processes which lead to cumulative genetic alterations in the long term period of virus bearing in carriers. In the HBV acute or immune-clearance infection phase, liver manifests immune response-induced necroinflammation and consequently hepatocyte regeneration. In the chronic hepatitis phase, the virus titers usually decrease, which attenuates liver inflammation, but it often accompanies with viral genome integration (10). With continuous expression of viral genes from host genomes, a large portion of these chronic viral hepatitis progresses into liver cirrhosis and dysplasia and, ultimately, hepatocellular carcinoma. In this process, the viral proteins are believed to be important players, which cross-talk with various host proteins to regulate the mechanism of hepatocellular carcinogenesis (11). A number of HBV gene products have been identified as viral oncoproteins. The viral transactivating protein HBx causes deregulation of cell cycle genes p53 and p21$^{Waf1}$ and activates the c-myc and c-jun oncoproteins (11,12). It also binds the DNA repair DNA damage-binding 1 (DDB1) protein and inhibits its activity (13). In addition, the pre-S$_2$ mutant LHBS, partially deleted of approximate 18 amino acids in the pre-S$_2$ region of the protein, was first identified in the type II ground glass hepatocytes (GGH), which were the histological hallmarks of hepatocytes in advanced stages of chronic HBV infection (2,3). It was (14, 15) found that HBV carriers who presented with pre-S$_2$ deletion mutant LHBS in sera were predisposed to advanced liver diseases, including liver cirrhosis and HCC. Our recent findings (16) also indicated that type II GGH was correlated with the increased tumor recurrence in and the decreased survival rates of patients with HCC undergoing hepatectomy. These findings invariably demonstrated that pre-S$_2$ visualize the pre-S mutant ones. The ELISA system developed in this study has allowed us to directly detect the high-risk pre-S$_2$ deletion mutants in serum using a one-step detection method, which has greatly improved the effectiveness. With this convenient tool, we will continue to detect the pre-S$_2$ mutant LHBS in larger populations of HBV chronic carriers and to evaluate the association of pre-S$_2$ deletion mutant with clinical outcomes in various stages of liver diseases including cirrhosis and HCC. A recent study has also found that the pre-S$_2$ deletion mutants increased after anti-viral therapies in chronic HBV carriers, suggesting that the carriers presenting the pre-S$_2$ mutant large HBV surface (LHBS) protein are the ones in high risk to HCC (17). Therefore, the detection of pre-S$_2$ deletion mutants in serum is important to predict HCC development or recurrence after surgery, especially in the cases after anti-viral treatments. The ELISA system developed in this study can provide a rapid and accurate method for detecting deletions in the HBV Pre-S region, thereby assessing a HBV carrier's risk of developing cirrhosis/HCC.

In an embodiment, patients who are HBeAg-negative and with viral load higher than 10$^4$ copies/ml are considered to be high risk groups. These patients should be tested for pre-S$_2$ deletion mutants. Briefly, LHBS protein and WT LHBS protein in patients who are HBeAg-negative with viral load higher than 10$^4$ copies/ml were detected by the ELISA method described above, and the amount of the pre-S$_2$ deletion mutant LHBS protein was calculated by subtracting the amount of the WT LHBS protein from that of the LHBS protein, as shown in Table 1. If the patients are HBV carriers with the pre-S$_2$ deletion mutant LHBS protein, the patients would be considered as high risk group of developing hepatocellular carcinoma (HCC) or cirrhosis, comparing to those who don't.

In another embodiment, patients who have persistence of surface antigens or HBV DNA after antiviral therapy for 3 months represent the presence of pre-S$_2$ deletion mutants and the high risk group to develop HCC. These patients should be tested for serum HBV pre-$S_2$ deletion mutants. Similarly, LHBS protein and WT LHBS protein in patients who have persistence of surface antigens or HBV DNA after antiviral therapy for 1-12 month(s), preferably 1-5 month(s), more preferably 3 months, were detected by the ELISA method described above, and the amount of the pre-$S_2$ deletion mutant LHBS protein was calculated by subtracting the amount of the WT LHBS protein from that of the LHBS protein, as shown in Table 1. If the patients after antiviral therapy carry the pre-$S_2$ deletion mutant LHBS protein, the patients would be considered as high risk group of developing hepatocellular carcinoma (HCC) or cirrhosis, comparing to those who don't.

In still another embodiment, patients receiving hepatectomy surgery for HBV-related HCC will be screened for the pre-$S_2$ deletion mutants in serum 3 months after surgery. Evaluating ground glass hepatocytes will be done simultaneously to assess the risk of HCC recurrence or de novo HCC development. The presence of pre-$S_2$ deletion mutants in serum and GGHs in liver tissues are considered to have increased risk of HCC recurrence. Similarly, LHBS protein and WT LHBS protein in patients receiving hepatectomy surgery for HBV-related HCC were detected by the ELISA method described above, and the amount of the pre-$S_2$ deletion mutant LHBS protein was calculated by subtracting the amount of the WT LHBS protein from that of the LHBS protein, as shown in Table 1. If the patients after surgery carry the pre-$S_2$ deletion mutant LHBS protein, the patients would be considered as high risk group of cancer recurrence, comparing to those who don't.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

---

What is claimed is:

1. A large hepatitis B virus surface protein-specific antibody, specifically binding to a recombinant protein shown as the amino acid sequence of SEQ ID NO: 1, wherein the antibody is produced by the hybridoma cell line deposited on Oct. 31, 2014 under accession number DSM ACC3253 at Leibniz-Institut DSMZ-Deutsche Sammlung von Mikroorganismen and Zellkulturen GmbH (DSMZ), Inhoffenstr. 7B, 38124 Braunschweig, Germany.

2. The antibody of claim 1, wherein the antibody is produced by the hybridoma cell line also deposited on Sep. 1, 2014 under accession number BCRC960490 at the Food Industry Research and Development Institute, 331 Shih-Pin Road, Hsinchu 300, Taiwan.

3. The antibody of claim 1, wherein the hybridoma cell line is fused by myeloma cells and splenocyte of mice immunized with the recombinant protein shown as the amino acid sequence of SEQ ID NO: 1.

4. The antibody of claim 1, further comprising a signal generating unit conjugated to the antibody, and the signal generating unit comprising a radioactive marker, a fluorescent marker, a phosphorescent marker, a chemiluminescent marker or a labeling enzyme.

5. The antibody of claim 4, wherein the labeling enzyme comprises a horse radish peroxidase or an alkaline phosphatase.

6. A wild type large hepatitis B virus surface protein-specific antibody, specifically binding to a peptide shown as the amino acid sequences of SEQ ID NO: 2, wherein the antibody is produced by the hybridoma cell line deposited on Oct. 31, 2014 under accession number DSM ACC3251 at Leibniz-Institut DSMZ-Deutsche Sammlung von Mikroorganismen and Zellkulturen GmbH (DSMZ), Inhoffenstr. 7B, 38124 Braunschweig, Germany.

7. The antibody of claim 6, wherein the antibody is produced by the hybridoma cell line also deposited on Jul. 16, 2014 under accession number BCRC960488 at the Food Industry Research and Development Institute, 331 Shih-Pin Road, Hsinchu 300, Taiwan.

8. The antibody of claim 6, wherein the hybridoma cell line is fused by myeloma cells and splenocyte of mice immunized with the peptide shown as the amino acid sequences of SEQ ID NO: 2.

9. The antibody of claim 6, further comprising a signal generating unit conjugated to the antibody, and the signal generating unit comprising a radioactive marker, a fluorescent marker, a phosphorescent marker, a chemiluminescent marker or a labeling enzyme.

10. The antibody of claim 9, wherein the labeling enzyme comprises a horse radish peroxidase or an alkaline phosphatase.

11. A hepatitis B virus surface protein-specific antibody, specifically binding to a recombinant protein shown as the amino acid sequence of SEQ ID NO: 3, wherein the antibody is produced by the hybridoma cell line deposited on Oct. 31, 2014 under accession number DSM ACC3252 at Leibniz-Institut DSMZ-Deutsche Sammlung von Mikroorganismen and Zellkulturen GmbH (DSMZ), Inhoffenstr. 7B, 38124 Braunschweig, Germany.

12. The antibody of claim 11, wherein the antibody is produced by the hybridoma cell line also deposited on Oct. 22, 2014 under accession number BCRC960491 at the Food Industry Research and Development Institute, 331 Shih-Pin Road, Hsinchu 300, Taiwan.

13. The antibody of claim 11, wherein the hybridoma cell line is fused by myeloma cells and splenocyte of mice immunized with the recombinant protein shown as the amino acid sequence of SEQ ID NO: 3.

14. An immunoassay kit for detecting large hepatitis B virus surface protein and wild type large hepatitis B virus surface protein in a biological sample, comprising:
   a substrate;
   a first antibody immobilized on the substrate, and the first antibody specifically binding to amino acid residues 1-226 of hepatitis B virus surface protein;
   a blocking solution for blocking an unconjugated portion;
   a second antibody specifically binding to amino acid residues 1-119 of large hepatitis B virus surface protein and a third antibody specifically binding to amino acid residues 125-142 of large hepatitis B virus surface protein; wherein the first antibody is a hepatitis B virus surface protein-specific antibody produced by a hybridoma cell line deposited on Oct. 31, 2014 under accession number DSM ACC3252 at Leibniz-Institut DSMZ-Deutsche Sammlung von Mikroorganismen und Zellkulturen GmbH (DSMZ), Inhoffenstr. 7B, 38124 Braunschweig, Germany, or progeny thereof, the second antibody is a large hepatitis B virus surface protein-specific antibody produced by a hybridoma cell line deposited on Oct. 31, 2014 under accession number DSM ACC3253 at Leibniz-Institut DSMZ-Deutsche Sammlung von Mikroorganismen und Zellkulturen GmbH (DSMZ), Inhoffenstr. 7B, 38124 Braunschweig, Germany, or progeny thereof, and the third antibody is a wild type large hepatitis B virus surface protein-specific antibody produced by a hybridoma cell line deposited on Oct. 31, 2014 under accession number DSM ACC3251 at Leibniz-Institut DSMZ-Deutsche Sammlung von Mikroorganismen und Zellkulturen GmbH (DSMZ), Inhoffenstr. 7B, 38124 Braunschweig, Germany, or progeny thereof; and
   a reaction substrate for reacting with a signal generating unit conjugated to the second and the third antibodies.

15. The immunoassay kit of claim 14, wherein the first antibody is a hepatitis B virus surface protein-specific antibody produced by a hybridoma cell line also deposited on Oct. 22, 2014 under accession number BCRC960491 at the Food Industry Research and Development Institute, 331 Shih-Pin Road, Hsinchu 300, Taiwan, or progeny thereof, the second antibody is a large hepatitis B virus surface protein-specific antibody produced by a hybridoma cell line also deposited on Sep. 1, 2014 under accession number BCRC960490 at the Food Industry Research and Development Institute, 331 Shih-Pin Road, Hsinchu 300, Taiwan, or progeny thereof, and the third antibody is a wild type large hepatitis B virus surface protein-specific antibody produced by a hybridoma cell line also deposited on Jul. 16, 2014 under accession number BCRC960488 at the Food Industry Research and Development Institute, 331 Shih-Pin Road, Hsinchu 300, Taiwan, or progeny thereof.

16. The immunoassay kit of claim 14, wherein the blocking solution comprises skim milk, bovine serum albumin, or casein.

17. The immunoassay kit of claim 14, further comprising a wash solution, wherein the wash solution comprises PBS, TBS, PBS including a detergent, or TBS including a detergent.

18. The immunoassay kit of claim 14, wherein the reaction substrate is tetramethylbenzidine (TMB) if the signal generating unit is a horse radish peroxidase.

* * * * *

SEQUENCE LISTING

<160> NUMBER OF SEQ ID NOS: 3

<210> SEQ ID NO 1
<211> LENGTH: 119
<212> TYPE: PRT
<213> ORGANISM: Hepatitis B virus

<400> SEQUENCE: 1

```
Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Val
        35                  40                  45

Lys Asp Asp Trp Pro Ala Ala Asn Gln Val Gly Val Gly Ala Phe Gly
    50                  55                  60

Pro Arg Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala
        115
```

<210> SEQ ID NO 2
<211> LENGTH: 18
<212> TYPE: PRT
<213> ORGANISM: Hepatitis B virus

<400> SEQUENCE: 2

```
Thr Ala Phe His Gln Thr Leu Gln Asp Pro Arg Val Arg Gly Leu Tyr
1               5                   10                  15

Leu Pro
```

<210> SEQ ID NO 3
<211> LENGTH: 226
<212> TYPE: PRT
<213> ORGANISM: Hepatitis B virus

<400> SEQUENCE: 3

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25              30

Asp Ser Trp Trp Thr Ser Leu Asn Phe Leu Gly Gly Thr Thr Val Cys
        35              40              45

Leu Gly Gln Asn Ser Gln Ser Pro Thr Ser Asn His Ser Pro Thr Ser
        50              55              60

Cys Pro Pro Thr Cys Pro Gly Tyr Arg Trp Met Cys Leu Arg Arg Phe
65              70                  75                      80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100             105             110

Ser Ser Thr Thr Ser Thr Gly Pro Cys Arg Thr Trp Thr Thr Pro Gly
        115             120             125

Gln Gly Thr Ser Met Tyr Pro Ser Trp Cys Trp Thr Lys Pro Leu Asp
        130             135             140

Gly Asn Cys Thr Cys Ile Pro Ile Pro Ser Ser Trp Ala Phe Gly Lys
145             150             155                     160

Phe Leu Trp Glu Trp Ala Ser Ala Arg Phe Ser Trp Leu Ser Leu Leu
            165             170             175

Val Pro Phe Val Gln Trp Phe Val Gly Leu Ser Pro Thr Val Trp Leu
            180             185             190

Ser Val Ile Trp Met Met Trp Tyr Trp Gly Pro Ser Leu Tyr Ser Ile
        195             200             205

Leu Ser Pro Phe Leu Pro Leu Leu Pro Ile Phe Phe Cys Leu Trp Val
    210             215             220

Tyr Ile
225
```